United States Patent
Frater et al.

(10) Patent No.: US 6,242,413 B1
(45) Date of Patent: Jun. 5, 2001

(54) BICYCLIC ALDEHYDE AND KETONE ODORANTS

(75) Inventors: Georg Frater, Winterthur; Philip Kraft, Dübendorf, both of (CH)

(73) Assignee: Givaudan Roure (International) S.A., Geneva (CH)

( * ) Notice: Subject to any disclaimer, the term of this patent is extended or adjusted under 35 U.S.C. 154(b) by 0 days.

(21) Appl. No.: 09/324,335

(22) Filed: Jun. 2, 1999

(30) Foreign Application Priority Data

Jun. 3, 1998 (CH) .................................................. 1202/98

(51) Int. Cl.[7] .............................. A61K 7/46; C07C 45/45; C07C 47/44; C07C 49/547
(52) U.S. Cl. .................................... 512/9; 512/9; 512/17; 568/343; 568/374; 568/375; 568/356; 568/445; 568/446; 585/360
(58) Field of Search ...................... 512/17, 9, 8; 585/360; 568/374, 343, 375, 356, 445, 446

(56) References Cited

U.S. PATENT DOCUMENTS

| | | | |
|---|---|---|---|
| 4,522,748 | 6/1985 | Maurer et al. | 252/522 R |
| 5,077,275 | 12/1991 | Boden et al. | 512/17 |

OTHER PUBLICATIONS

Kraft, P., *Synthesis*, 4:695–703 (1999).
Posner, G., et al., *Tetrahedron Letters*, 27(6):659–662 (1986).
Alpoim, M., *Tetrahedron Letters*, 29(33):4173–6 (1988).
Calkin, R.R. et al., "Perfumery–Practice and Principles," Wiley, New York 1994, pp. 138–140.
van Straten, J.W., "A convenient and general synthesis of 1,2–dimethylenecycloalkanes" Recueil, Journal of the Royal Netherlands Chemical Society, Apr. 1997, 1978, pp. 105–106.
Ruder, S.M. et al., "2–Chloroethyl Dimethyl Sulfonium Iodine," Pergamon Press Ltd., 1984, pp. 5501–5504.
Herz, W. et al., "Photooxygenation of 1–Vinycycloalkenes. The Competition between "Ene" Reaction and Cycloaddition of Singlet Oxygen," J.Org. Chem. vol. 50, 1985, pp. 618–627.

*Primary Examiner*—Sreeni Padmanabhan
(74) *Attorney, Agent, or Firm*—Mark E. Waddell; Stephan M. Haracz; Bryan Cave LLP

(57) ABSTRACT

The invention relates to bicyclic aldehydes and ketones of formula (I):

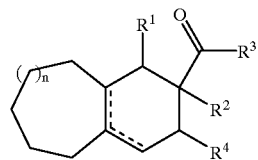

wherein
n is 1 or 2;
$R^1$ and $R^4$ are independently H or $CH_3$; and
$R^2$ and $R^3$ are independently H, $CH_3$ or $CH_2CH_3$ The invention also provides odorant compositions containing at least one compound of formula (I). A process for the manufacture of $R^1$-methyl substituted compounds of formula (I) having a bridgehead-positioned double bond, as well as intermediates thereof is also provided.

15 Claims, No Drawings

BICYCLIC ALDEHYDE AND KETONE ODORANTS

FIELD OF THE INVENTION

The invention provides aldehydes and ketones having a bicyclo[6.4.0]dodec-1(8)-en-10-yl, bicyclo[5.4.0]undec-1(7)-en-9-yl, bicyclo[6.4.0]dodec-1(12)-en-10- yl or bicyclo[5.4.0]undec-1(11)-en-9-yl skeleton, especially 1-{bicyclo[6.4.0]dodec-1(8)-en-10-yl}ethan-1-ones, 1-{bicyclo[6.4.0]dodec-1(8)-en-10-yl}methanals, 1- {bicyclo[5.4.0]-undec-1(7)-en-9-yl}ethan-1-ones, 1-{bicyclo[5.4.0]undec-1(7)-en-9-yl}methanals, 1-{bicyclo[6.4.0]dodec-1(12)-en-10-yl}ethan-1-ones, 1-{bicyclo[6.4.0]dodec-1(12)-en-10-yl}methanals, 1-{bicyclo[5.4.0]undec-1(11)-en-9-yl}ethan-1-ones and 1-{bicyclo[5.4.0]-undec-1(12)-en-9-yl}methanals, which can be methyl- or ethyl-substituted on the six-membered ring, as well as their use as odorants.

BACKGROUND OF THE INVENTION

Ionones and their linear derivatives (for example, Raldeine® or Timberol®), as well as their cyclic derivatives (for example, Iso E Super®) play a central role in perfumery. In particular, in the last ten years the classical perfumes with top, middle and base notes have been superseded more and more by monolithic creations, which are build around a main accord from relatively few olfactory substances of which some can be present in an amount of up to 25% and more in a composition [R. R. Calkin, J. S. Jellinek, Perfumery—Practice and Principles, Wiley, New York 1994, 138–140].

Ionones and their derivatives are preferred olfactory substances for the composition of such accords and perfumes, as they combine harmonically with a large number of olfactory building blocks, confer transparency and warmth to the compositions and their soft, floral-woody notes themselves remain pleasant in high concentration.

On the other hand, ionones and ionone derivatives are a relatively old class of odorant substances and although they cover an entire spectrum from fresh floral to strong woody-amber like facets, there exists, however, a great need for novel compounds of similar tonality, but with new, individual olfactory characters in order to create new original accords which, in turn, can be used as components of new trend perfumes (for example, the so-called "sheer orientals").

SUMMARY OF THE INVENTION

In one embodiment the invention is a compound of formula (I):

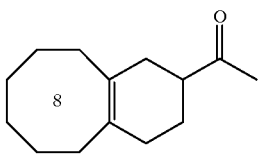

wherein
  n is 1 or 2;
  $R^1$ and $R^4$ are independently H or $CH_3$; and
  $R^2$ and $R^3$ are independently H, $CH_3$ or $CH_2CH_3$.

Another embodiment of the invention is a compound having formula (I'):

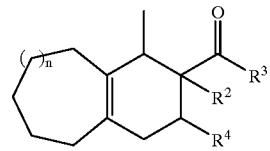

wherein
  n is 1 or 2;
  $R^4$ is H or $CH_3$; and
  $R^2$ and $R^3$ are independently H, $CH_3$ or $CH_2CH_3$.

Another embodiment of the invention is a process for producing a $R^1$-methyl substituted compound of formula (I'). This process includes reacting a spirocyclic vinylcyclopropane compound with a dienophile in the presence of a catalyst; and then producing regioselectively or Z-diastereoselectively, the compound of formula (I).

DETAILED DESCRIPTION OF THE INVENTION

In aldehydes and ketones having the bicyclo skeleton indicated in more detail below there has now been found a class of compounds which enriches the woody-floral olfactory spectrum of ionones and ionone derivatives by new facets and thereby satisfies the aforementioned requirements in an advantageous manner. This novel class of compounds is represented by formula (I):

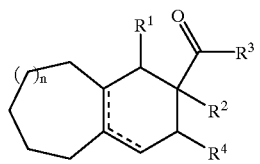

wherein
  n is 1 or 2;
  $R^1$ and $R^4$ are independently H or $CH_3$; and
  $R^2$ and $R^3$ are independently H, $CH_3$ or $CH_2CH_3$ The dotted line in formula (I) signifies a double bond between the two bridgehead atoms or between bridgehead atom 1 and ring atom 11 or 12.

The compounds of formula (I) are novel. Formula (I) accordingly embraces aldehydes, as well as methyl ketones and ethyl ketones with bicyclo[6.4.0]dodec-1(8)-en-10-yl or bicyclo[5.4.0]undec-1(7)-en-9-yl substituents or, respectively, bicyclo[6.4.0]dodec-1(12)-en-10-yl or bicyclo[5.4.0]undec-1(11 )-en-9-yl substituents, which can carry methyl or ethyl substituents on the cyclohexene ring. The following compounds numbered 1–14 are preferred examples of this novel class of compounds:

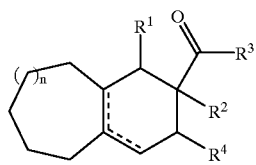

-continued

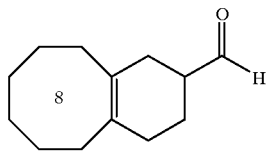
2

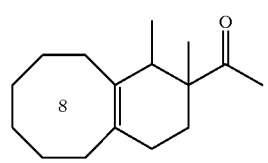
3

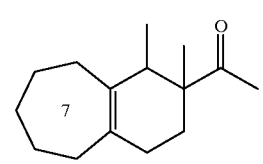
4

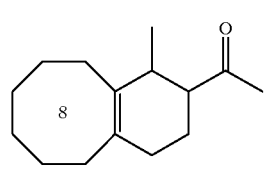
5

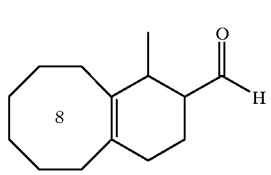
6

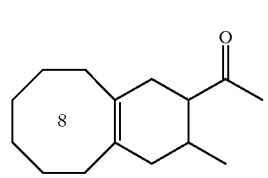
7

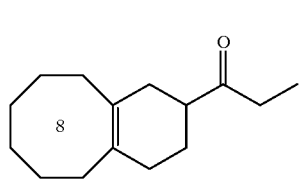
8

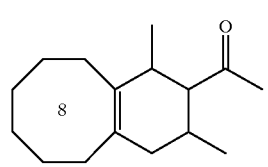
9

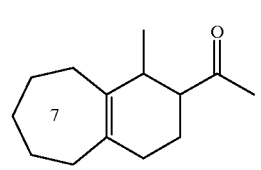
10

-continued

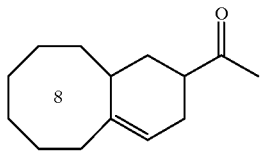
11

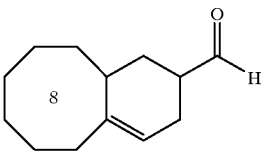
12

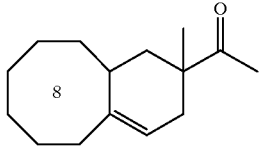
13

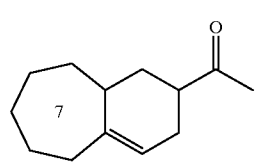
14

The compounds set forth above 1–14 are exemplary only and are not intended to limit the scope of the present invention in any way.

The compounds of formula (I) have woody-flowery notes, which are reminiscent of ionones, and in addition aldehydic, maritime, amber- and tobacco-like, to some extent also fruity-fresh, melon-like, or balsamic side-notes. In some cases, such as for example, in the case of compounds 3 and 4, the woody character dominates strongly and the total olfactory impression is woody-amber like to dry-frankincense like, reminiscent of Iso E Super®, as well as of vetiver oil.

In addition to compounds 3 and 4, the present invention also includes perfumistically aldehyde compounds, for example compounds 2 and 6, as well as the $R^1$-methyl substituted compounds 5 and 10.

The compounds of formula (I), preferably compounds 1–13, are intended to embrace, in accordance with the invention, all possible stereomers and diastereomers of the respective compounds. In some instances, the compounds of the present invention differ greatly in their intensity and in their odor, but on the basis of their odor each of them can be used perfumistically. In the examples which follow, the respective olfactory intensity and interesting diastereomers are described and characterized in more detail.

The compounds of formula (I) harmonize with a large number of natural and/or synthetic raw materials which are frequently used in odorant compositions. Especially in the floral and chypre olfactory directions interesting accords and perfumes can be synthesized around the compounds of formula (I). The compounds of formula (I), however, are outstandingly suitable for monolithic compounded perfumes of oriental-amber like olfactory directions. Further, new accentuated woody compositions such as, for example, of the "Féminitdu Bois" (Shiseido 1992) type can be synthesized very advantageously with the compounds of formula (I).

In the present invention, use of the compounds of formula (I) is not limited to these types of perfume, or to special olfactory directions, odorant derivatives or classes of chemical substances. For example, classes of substances which harmonize especially well (i.e., may be combined) with the compounds of formula (I) include:

| | |
|---|---|
| Ethereal oils and extracts, e.g. | bay oil, bergamot oil, cedarwood oil, geranium oil, guaiac wood oil, patchouli oil, petitgrain oil, rose oil, rosewood oil, vetiver oil, ylang-ylang oil; |
| Alcohols, e.g. | citronellol, Dimetol®, Ebanol®, cis-3-hexenol, geraniol, linalool, Peonile®, phenoxanol, Rosalva®, Rosaphen®, Sandalore®, cinnamic alcohol; |
| Aldehydes and ketones, e.g. | alpha-amylcinnamaldehyde, Cashmeran®, beta-damascenone, Dupical®, Florhydral®, Frambinon®, Givescone®, Hedion®, hydroxycitronellal, Lilial®, vanillin; |
| Ethers and acetals, e.g. | Ambrox®, Calone®, Galaxolide®, Magnolan®, Rhubafuran®, rose oxide, Spirambrene®; |
| Esters and lactones, e.g. | Agrumex®, benzyl acetate, benzyl salicylate, citronellyl acetate, delta- and gamma-decalactone, gamma-undecalactone; |
| Macrocycles, e.g. | Ambrettolide®, Ambretone®, muscone, musk R-1, Thibetolide®, Trimofix O®; |
| Heterocycles, e.g. | indole, skatole. |

The synthesis of the compounds of formula (I) may be effected on the one hand, as is set forth in more detail in Examples 1 and 11, by Diels-Alder reaction of the corresponding bis(methylene)cycloalkanes, ethylidenemethylenecycloalkanes or 1-vinylcycloalkenes, accessible, for example, according to J. W. van Straten, J. J. van Norden, T. A. M. van Schaik, G. T. Franke, W. H. de Wolf, F. Bickelhaupt [Recl. Trav. Chim. Pays-Bas 1978, 97, 105] or W. Herz and R.-R. Juo [J. Org. Chem. 1985, 50, 618] which are hereby incorporated by reference as if they were recited in full herein.

Alternatively, in the present invention there has now been found for the $R^1$-methyl substituted compounds of formula (I) having a bridgehead-positioned double bond (formula (I')), a novel synthesis route via vinylcyclopropanes (V), which is set forth in more detail in example 6. In this example, 4-methylenespiro[2.7]decane and 4-methylenespiro[2.6]nonane are accessible from spiro[2.7] decan-4-one and spiro[2.6]nonan4-one, respectively, for example, by a Wittig reaction. These compounds are heated under reflux for several hours to a few days with a catalyst, preferably the Wilkinson catalyst, in a high-boiling, relatively non-polar solvent, such as for example, toluene or xylene. The compounds of formula (I') are then isolated regioselectively and in some cases, as in example 6, also Z-diastereoselectively as the main product of this novel reaction.

The starting materials spiro[2.7]decan-4-one and spiro [2.6]nonan-4-one are readily accessible according to the procedure described by S. M. Ruder, R. C. Ronald [Tetrahedron Lett. 1984, 25, 5501], which is hereby incorporated by reference as if recited in full herein. This route is an attractive alternative for the synthesis of the formula (I') compounds via exocyclic dienes as set forth below:

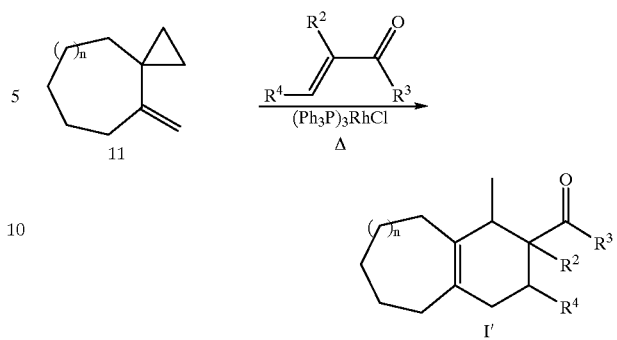

wherein
n is 1 or 2
$R^4$ is H or $CH_3$; and
$R^2$ and $R^3$ are independently H, $CH_3$ or $CH_2CH_3$.

A further advantage of this process is that the intermediates V in which n is 1 or 2 are themselves novel, interesting fresh, green-minty, somewhat woody-fruity odorants, which likewise can be used in perfumery.

The following examples are provided to further illustrate the synthesis of various compounds within the scope of the present invention, as well as certain physical properties of such compounds. These examples are illustrative only and are not intended to limit the scope of the invention in any way.

EXAMPLES

Example 1

Synthesis of 1-{Bicyclo[6.4.0]dodec-1'(8')-en-10'-yl}ethan-1-one (1)

The starting material, 1,2-bis(methylene)cyclooctane, was prepared according to the procedure set forth in J. W. van Straten, J. J. van Norden, T. A. M. van Schaik, G. T. Franke, W. H. de Wolf, F. Bickelhaupt [Recl. Trav. Chim. Pays-Bas 1978, 97, 105].

1.46 ml (17.8 mmol) of but-3-en-2-one was added with stirring to a solution of 2.00 g (14.7 mmol) of 1,2-bis (methylene)cyclooctane in 20 ml of dry toluene and the reaction mixture was cooled to 0° C. At this temperature, 160 mg (1.20 mmol, 7 mol %) of aluminum trichloride was added to the mixture under nitrogen. After stirring at 0° C. for 5 minutes, the reaction mixture was stirred continuously and allowed to warmn to room temperature for 60 hours under nitrogen. Thereafter, the mixture was poured into 400 ml of tert-butyl methyl ether/water (1:1). The organic phase was separated and the aqueous phase was extracted three times with 200 ml of tert-butyl methyl ether. The organic phases were combined, dried over sodium sulfate and concentrated on a rotary evaporator. After flash chromatography (n-pentane/tert-butyl methyl ether, 20:1, $R_f$=0.58) on silica gel, there was obtained 2.54 g (84%) of 1-{bicyclo[6.4.0] dodec-1'(8')-en-10'-yl}ethan-1-one (1) as a colorless liquid with the following properties:
Odor: Woody-flowery after β-ionone, fruity-fresh, slightly aldehydic and amber-like.—IR (film): ν=1711 cm$^{-1}$ (νC=O);—$^1$H-NMR (CDCl$_3$): δ=1.35–1.57 (m, 10H, 3'-H$_2$-6'-H$_2$, 11'-H$_2$), 2.18(s, 3H, 2-H$_3$), 1.93–2.14(m, 8H, 2'-,7'-,9'-,12'-H$_2$), 2.55 (dddd, J 11.5, 10.1, 5.3, 2.8 Hz, 1H, 10'-H);—$^{13}$C-NMR (CDCl$_3$): δ=25.29 (t, C-11'), 26.47/26.48 (t, C-3',-6'), 27.88 (q, C-2), 28.71/28.81 (t, C-4',-5'), 29.07/31.05 (t, C-4',-5'), 29.07/31.05 (t, C-2',-7'), 31.54/31.70 (t, C-9', -12), 48.19 (d, C-10'), 128.79 (s, C-1'), 130.27 (s, C-8'), 211.86 (s, C-1);—MS (EI): m/z (%)=43 (87) [$C_2H_3O^+$], 67 (100) [$C_5H_7^+$], 81 (68) [$C_6H_9^+$], 93 (20)/107 (15)/121 (15)/135 (7)/149 (5) [$C_nH_{(2n-5)}^+$series], 163 (49) [$M^+—C_2H_3O$], 191 (4) [$M^+—CH_3$], 206(23) [$M^+$];—$C_{14}H_{22}O$ (206.33): calc. C, 81.50, H 10.75; found C, 81.49, H, 10.57.

The compounds of examples 2–5 were synthesized using the same procedure as set forth in example 1 for 1,2-bis (methylene)-cyclooctane. Accordingly, examples 2–5 below set forth only the olfactory characteristics, the spectroscopic data and in some cases, the elementary analysis of the final products.

Example 2

Synthesis of 1-{Bicyclo[6.4.0]dodec-1'(8')-en-10'-yl}methanal (2)

Odor: Maritime, reminiscent of watermelons, tobacco or cigarette-like and somewhat ionone like-fruity.—IR (film): $v=1726$ cm$^{-1}$ (v HC=O);—$^1$H-NMR (CDCl$_3$): δ=1.41–1.65 (m, 10H, 3'-H$_2$-6'-H$_2$, 11'-H$_2$), 1.93–2.13 (m, 8H, 2'-,7'-,9'-,12'-H$_2$), 2.47 (m$_c$, 1H, 10'-H), 9.69 (d, J 1.2 Hz, 1H, CHO);—$^{13}$C-NMR (CDCl$_3$): δ=22.78 (t, C-11'), 26.49/26.52 (t, C-3',-6'), 27.99/28.52 (t, C-4',-5'), 28.79/28.81 (t, C-2',-7'), 31.70/31.77 (t, C-9',-12'), 46.81 (d, C-10'), 128.43 (s, C-1'), 130.82 (s, C-8'), 204.82 (d, C-1);—MS (EI): m/z (%) =29 (33) [CHO], 41(72) [$C_3H_5^+$], 67 (90) [$C_5H_7^+$], 91 (98) [$C_7H_7^+$], 107 (51)/121 (34)/135 (29)/149 (12) [$C_nH_{(2n-5)}^+$ series], 164 (31) [$M^+$-CO], 192 (100) [$M^+$].

Example 3

Synthesis of 1-{10'-Methylbicyclo[6.4.0]dodec-1'(8')-en-10'-yl}methanal (6)

Odor: Fruity-ionone like, amber- and tobacco-like, with a watermelon note.—IR (film): v=1727 cm$^{-1}$ (v HC=O).—$^1$H-NMR (CDCl$_3$): δ=1.04(s, 3H, 10'-Me), 1.37–1.54 (m, 10H, 3'-H$_2$-6'-H$_2$, 11'-H$_2$), 1.78 (d, J 16.0 Hz, 1H, 9'-H$_b$), 2.01–2.12 (m, 6H, 2'-,7'-,12'-H$_2$), 2.29 (d, J 16.0 Hz, 1H, 9'-H$_a$), 9.47 (s, 1H, CHO);—$^{13}$C-NMR (CDCl$_3$): δ=20.68 (q, 10'-Me), 26.42/26.48/26.61 (t, C-3',-6',-11'), 28.80/28.91 (t, C-4',-5'), 29.09 (t, C-12'), 31.63/31.86 (t, C-2',-7'), 35.88 (t, C-9'), 45.08 (s, C-10'), 128.17 (s, C-1'), 130.07 (s, C-8') 206.19 (d, C-1);—MS (EI): m/z (%)=29 (36) [CHO], 41 (78) [$C_3H_5^+$], 67 (65) [$C_5H_7^+$], 81 (100) [$C_6H_9^+$], 95 (61) [$C_7H_{11}^+$], 121 (39)/135 (29)/149 (20)/163 (28) [$C_nH_{(2n-5)}^+$ series], 177 (70) [$M^+$-CHO], 191 (9) [$M^+$-CH$_3$], 206(31) [$M^+$].

Example 4

Synthesis of (r-10',c-11')-1-{11-'-Methylbicyclo[6.4.0]dodec-1'(8')-en-10'-yl}ethan-1-one (7)

Odor: Woody, ionone-like, somewhat reminiscent of coffee.—IR (film): v=1710 cm$^{-1}$ (vC=O); —$^1$H-NMR (CDCl$_3$): δ=0.93 (d, J 6.4 Hz, 3H, 11'-Me), 1.35–1.55 (m, 8H, 3'-H$_2$-6'-H$_2$), 1.76–2.16 (m, 9H, 2'-,7'-,9'-, 12'-H$_2$, 11'-H$_{ax}$), 2.17 (s, 3H, 2-H$_3$), 2.36 (ddd, J 10.3, 10.3, 5.4 Hz, 1H, 10'-H$_{ax}$);—$^{13}$C-NMR (CDCl$_3$): δ=19.48 (q, 11'-Me), 26.44/26.25 (t, C-3',-6'), 28.70/28.74 (t, C-4',-5'), 29.21 (q, C-2), 30.83 (d, C-11'), 31.30/31.42/32.47 (t, C-2',-7',-9'), 37.78 (t, C-12'), 55.17(d, C-10'), 128.26 (s, C-1), 129.95 (s, C-8'), 213.01 (s, C-1);—MS (EI): m/z (%)=43 (61) [$C_2H_3O^+$], 67 (100) [$C_5H_7^+$], 95 (63) [$C_7H_{11}^+$], 177 (52) [$M^+—C_2H_3O$], 205 (5) [$M^+—CH_3$], 220 (19) [$M^+$]; —$C_{15}H_{24}O$ (220.35): calc. C 81.76, H 10.98; found C 81.46, H 10.95.

Example 5

Synthesis of 1-{Bicyclo[6.4.0]dodec-1'(8')-en-10'-yl}propan-1-one (8)

Odor: Reminiscent of β-ionone, fruity-floral, fresh, somewhat pear-like.—IR (film): v=1711 cm$^{-1}$(v C=O);—$^1$H-NMR (CDCl$_3$): δ=1.06 (t, J 7.2 Hz, 3H, 3-H$_3$), 1.35–1.58 (m, 10H, 3'-H$_2$-6'-H$_2$, 11'-H$_2$), 1.99–2.18 (m, 8H, 2'-,7'-,9'-, 12'-H$_2$), 2.48 (dq, J 17.6, 7.3 Hz, 1H, 2-H$_b$), 2.54 (dq, J 17.6, 7.3 Hz, 1H, 2-H$_a$), 2.57 (dddd, J 11.6, 10.4, 5.2, 2.9 Hz, 1H, 10'-H);—$^{13}$C-NMR (CDCl$_3$): δ=7.68 (q, C-3), 25.45 (t, C-11'), 26.45/26.47 (t, C-3',-6'), 28.70/28.80 (t, C-4',-5'), 29.12/31.31 (t, C-2',-7'), 31.53/31.69 (t, C-9',-12'), 33.68 (t, C-2), 47.23 (d, C-10'), 128.90 (s, C-1'), 130.17 (s, C-8'), 214.31 (s, C-1);—MS (EI): m/z (%)=29 (33) [$C_2H_5^+$], 57 (40) [$C_3H_5O^+$], 67 (100) [$C_5H_7^+$], 81 (81) [$C_6H_9^+$],91 (29) [$C_7H_7^+$], 107 (13)/121 (15)/135 (5) [$C_nH_{(2n-5)}^+$ series], 163 (49) [$M^+—C_2H_5$-CO], 191 (16) [$M^+—C_2H_5$], 220 (18) [$M^+$];—$C^{15}H_{24}O$ (220.35): calc. C 81.76, H 10.98; found C 81.80, H 10.90.

Example 6

Synthesis of (r-9',c-10')-1-{9',10'-Dimethylbicyclo[6.4.0]dodec-1'(8')-en-10'-yl}ethan-1-one (3)

a) Preparation of the intermediate 4-methylenespiro[2.7]decane (V, n=2)

The starting material, spiro[2.7]decan-4-one, was prepared according to S. M. Ruder, R. C. Ronald [Tetrahedron Lett. 1984, 25, 5501] which is hereby incorporated by reference as if recited in full herein.

64.3 g (180 mmol) of methyltriphenylphosphonium bromide was added while stirring under nitrogen to a solution of 19.1 g (170 mmol) of potassium tert-butylate in 350 ml of dry tetrahydrofuran and the mixture was heated to reflux. Then, a solution of 22.8 g (150 mmol) of spiro[2.7]decan-4-one in 50 ml of dry tetrahydrofuran was added dropwise to the boiling reaction mixture. The mixture was heated under reflux for a further 2 hours. After cooling, the reaction mixture was poured into 1l of tert-butyl methyl ether/water (1:1). The organic phase was separated and the aqueous phase was extracted twice with 500 ml of tert-butyl methyl ether. The organic extracts were combined, dried over sodium sulfate and concentrated on a rotary evaporator. After flash chromatography (n-pentane, R$_f$=0.97) on silica gel, there was obtained 17.1 g (76%) of 4-methylenespiro [2.7]decane (V, n=2) as a colorless liquid with the following properties:

Odor: fresh minty, green-resinous, somewhat woody-fruity.—IR (film): v2922/2851/2997/3076 cm$^{-1}$ (vC-H), 1444 cm$^{-1}$ (δ H-C-H), 879/1014 cm$^{-1}$ (δ C=C—H), 1632 cm$^{-1}$ (vC=C);—$^1$H-NMR (CDCl$_3$): δ=0.45 (dd, J 5.8, 3.6 Hz, 2H, 2-H$_2$), 0.59 (dd, J 5.8, 4.0 Hz, 2H, 1-H$_2$), 1.45–1.59 (m, 8H, 7-H$_2$-10-H$_2$), 1.67–1.73 (m, 2H, 6-H$_2$), 2.25 (ddd, J 14.6, 6.4, 1.2 Hz, 2H, 5-H$_2$), 4.71 (dd, J 3.6, 1.2 Hz, 2H, 11-H$_2$);—$^{13}$C-NMR (CDCl$_3$): δ=14.85 (2t, C-1,-2), 25.00 (s, C-3), 25.24 (t, C-6), 26.38/26.41 (t, C-7,-8), 29.53 (t, C-9), 34.36 (t, C-5), 37.09 (t, C-10), 108.88 (t, C-11), 155.76 (s, C-4);—MS (EI): m/z (%)=67 (85) [$C_5H_7^+$], 79 (100)/93 (61)/107 (29)/121 (21)/135 (13) [$C_nH_{(2n-5)}^-$ series], 150 (3) [$M^+$].

b) Preparation of (r-9',c-10')-1-{9',10'-dimethylbicyclo[6.4.0]dodec-1'(8')-en-10'-yl}-ethan-1-one (3):

2.20 g (14.6 mmol) of 4-methylenespiro[2.7]decane was dissolved in 20 ml of dry toluene and treated under nitrogen with 550 mg (0.59 mmol, 4 mol %) of tris (triphenylphosphine)-rhodium(I) chloride. 1.80 ml (17.5 mmol) of 3-methyl-3-buten-2-one was introduced by injection while stirring under an inert gas atmosphere. The reaction mixture was heated to reflux for 40 hours. After cooling, the catalyst was separated by filtration over silica gel. The filtrate was poured into 400 ml of tert-butyl methyl ether/water (1:1) and the organic phase was separated. The aqueous phase was extracted three times with 200 ml of tert-butyl methyl ether and the organic extracts were subsequently combined. After drying over sodium sulfate, concentration on a rotary evaporator and flash chromatography (n-pentane/tert-butyl methyl ether, 40:1, $R_f$=0.41) on silica gel, there was obtained 1.62 g (47%) of (r-9',c-10')-1-{9', 10'-dimethylbicyclo[6.4.0]dodec-1'(8')-n-10'-yl}ethan-1-one (3) as a colorless solid with the following properties: Odor: Intensive woody-amber like, fresh-dry frankincense-like, reminiscent of Iso E Super® and of vetiver oil.—M.p. 56.3° C.;—IR (KBr): ν=1704 cm$^{-1}$ (ν C=O);—$^1$H-NMR (CDCl$_3$): δ=0.83 (d, J 6.8 Hz, 3H, 9'-Me), 1.10 (s, 3H, 10'-Me), 1.42–2.06 (m, 15H, 2'-,7'-H$_b$, 3'-H$_2$-6'-H$_2$, 9'-H, 11'-,12'-H$_2$), 2.14 (s, 2-H$_3$), 2.23–2.40 (m, 2H, 2'-,7'-H$_a$);—$^{13}$C-NMR (CDCl$_3$): δ=17.06 (q, 9'-Me), 21.04 (q, 10'-Me), 22.73 (t, C-11'), 25.36 (q, C-2), 26.62/26.67 (t, C-3',-6'), 26.98 (t, C-4'), 28.75 (t, C-5'), 29.73 (t, C-12'), 30.81 (t, C-7'), 31.68 (t, C-2'), 40.74 (d, C-9'), 49.86 (s, C-10'), 128.85 (s, C-1'), 133.09 (s, C-8'), 214.22 (s, C-1);—MS (EI): m/z (%)=95 (31) [C$_7$H$_{11}^+$], 191 (100) [M$^+$-C$_2$H$_3$O], 219 (3) [M$^+$-CH$_3$], 234(12) [M$^+$];—C$_{16}$H$_{26}$O (234.38): calc. C 81.99, H 11.18, O 6.83; found C 81.68, H 11.15, O 6.89.

The compounds of examples 7–10 were synthesized using the same procedure as set forth in example 6 for 4-methylenespiro[2.7]decane. Accordingly, examples 7–10 set forth only the olfactory description and the analytical data for the final products.

Example 7

(r-8',c-9')-1-{8',9'-Dimethylbicyclo[5.4.0]undec-1' (7')-en-9'-yl}ethan-1-one (4)

Odor: Woody-cedar like, vetiver, floral, sandalwood-like.— IR (film): ν=1703 cm$^{-1}$ (νC=O);—$^1$H-NMR (CDCl$_3$): δ=0.77 (d, J 6.8 Hz, 3H, 8'-Me), 1.06 (s, 3H, 9'-Me), 1.34–1.44 (m, 5H, 4'-H$_2$, 8'-H, 10'-H$_2$), 1.68–1.75 (m, 4H, 3'-,5'-H$_2$), 1.93–2.08 (m, 6H, 2', 6'-,11'-H$_2$), 2.11 (s, 3H, 2-H$_3$);—$^{13}$C-NMR (CDCl$_3$): δ=16.32 (q, 8'-Me), 20.59 (q, 9'-Me), 22.97 (t, C-10'), 25.39 (q, C-2), 26.26/26.82 (t, C-3',-5'), 28.83 (t, C-4'), 32.76 (t, C-11'), 34.40/34.58 (t, C-2',-6'), 43.34 (d, C-8'), 49.54 (s, C-9'), 132.12 (s, C-1'), 135.45 (s, C-7'), 214.14 (s, C-1);—MS (EI): m/z=43 (52) [C$_2$H$_3$O$^+$], 95 (100) [C$_7$H$_{11}^+$], 107 (40)/121 (32)/149 (4) [C$_n$H$_{(2n-5)}^+$ series], 177 (81) [M$^+$-C$_2$H$_3$O], 220 (7) [M$^+$].

Example 8

(r-9',c-10')-1-{9'-Methylbicyclo[6.4.0]dodec-1'(8')-en-10'-yl}ethan-1-one (5)

Odor: Woody, reminiscent of vetiver and β-ionone, with a slight amber note.—IR (film): ν=1709 cm$^{-1}$ (νC=O);—$^1$H-NMR (CDCl$_3$): δ=0.84 (J 6.8 Hz, 3H, 9'-Me), 1.39–1.61 (m, 8H, 3'-H$_2$-6'-H$_2$), 1.72 (m$_c$, 2H, 11'-H$_2$), 1.93–2.08 (m, 4H, 2'-H$_2$, 7'-,12'-H$_b$), 2.16 (s, 3H, 2-H$_3$), 2.19–2.31 (m, 2H, 7'-,12'-H$_a$), 2.52 (m$_c$, 1H, 9'-H), 2.56 (m$_c$, 1H, 10'-H);—$^{13}$C-NMR (CDCl$_3$): δ=14.65 (q, 9'-Me), 18.07 (t, C-11'), 26.38/ 26.90 (t, C-3',-6'), 28.39 (q, C-2), 28.46/29.20 (t, C4',-5'), 30.21/30.83 (t, C-2',-7'), 31.40 (C-12'), 34.50 (d, C-9'), 52.63 (d, C-10'), 130.53/134.38 (s, C-1',-8'), 211.46 (s, C-1);—MS (EI): m/z (%)=43 (65) [C$_2$H$_3$O$^+$], 81 (100) [C$_6$H$_9^+$], 95 (50) [C$_7$H$_{11}^+$], 177 (38) [M$^+$-C$_2$H$_3$O], 205 (3) [M$^+$-CH$_3$], 220 (14) [M$^+$];-C$_{15}$H$_{24}$O (220.35): calc. C, 81.76, H, 10.98; found C, 81.60, H, 10.87.

Example 9

(r-9',c-10', t-11')-1-{9',11'-Dimethylbicyclo[6.4.0] dodec-1'(8')-en-10'-yl}ethan-1-one (9)

Odor: Woody, balsamic, fruity, relatively weak and slightly reminiscent of ,β-ionone. -IR (film): ν=1710 cm$^{-1}$ (νC=O) ;—$^1$H-NMR (CDCl$_3$): δ=0.84 (d, J 7.2 Hz, 3H, 11'-Me), 0.91 (d, J 6.0 Hz, 3H, 9'-Me), 1.42–1.55 (m, 8H, 3'-H$_2$-6'-H$_2$), 1.67 (dd, J 16.8, 10.4 Hz, 1H, 12-H$_b$), 1.89–2.27 (m, 5H, 2'-H$_2$,7'-H$_2$,12'-H$_a$), 2.09 (m$_c$,1H, 11'-H$_{ax}$), 2.15 (s, 3H, 2-H$_3$), 2.37 (dq, J 6.0, 4.8 Hz, 1H, 9-H$_{eq}$), 2.45 (dd, J 11.1, 4.8 Hz, 1H, 10-H$_{ax}$);-$^{13}$C-NMR (CDCl$_3$): δ=15.30 (q, 9'-Me), 19.93 (q, 11'-Me), 23.85 (d, C-11'), 26.37/26.90 (t, C-3',-6'), 28.41 (t, C-5'), 30.14 (t, C-4'), 30.52 (q, C-2), 30.65 (t, C-7'), 31.23 (t, C-2'), 35.26 (d, C-9'), 38.46 (t, C-12'), 59.06 (d, C-10'), 129.88 (s, C-1'), 134.10 (s, C-8'), 211.05 (s, C-1);—MS (EI): m/z (%)=43 (68) [C$_2$H$_3$O$^+$], 95 (100) [C$_7$H$_{11}^+$], 109 (45) [C$_8$H$_{13}^+$], 191.1797 (38) [M$^+$-C$_2$H$_3$O], 219 (5) [M$^+$-CH$_3$],234 (11) [M$^+$].

Example 10

1-{8'-Methylbicyclo[5.4.0]undec-1'(7')-en-9'-yl}ethan-1-one (10)

Odor: Ionone-like, green-floral, woody, creamy.—IR (film): ν=1709 cm$^{-1}$ (νC=O), 1353/1376 cm$^{-1}$ (δ CH$_3$);—$^1$H-NMR (CDCl$_3$): δ=0.80 (d, 7.1 Hz, 3H, 8'-Me), 1.34-1.76 (m, 8H, 3'-H$_2$-5'-H$_2$,10'-H$_2$), 1.99–2.15 (m, 6H, 2'-,6'-,11'-H$_2$), 2.16 (s, 3H, 2-H$_3$), 2.45 (quint, J 6.2 Hz, 1H, 8'-H), 2.58 (ddd, J 12.1, 6.2, 3.2 Hz, 1H, 9'-H);—$^{13}$C-NMR (CDCl$_3$): δ=14.12 (q, 8'-Me), 18.26 (t, C-10'), 26.23/27.25 (t, C-3',-5'), 28.44 (q, C-2), 31.59/32.71 (t, C-2',-6'), 34.12/34.68 (t, C-4',-11'), 36.82 (d, C-8'), 52.32 (d, C-9'), 134.00/137.29 (s, C-1',-7'), 211.53 (s, C-1);—MS (EI): m/z (%)=28 (38) [CO$^+$], 43 (68) [C$_2$H$_3$O$^+$], 81 (100) [C$_6$H$_9^+$], 91 (34) [C$_7$H$_7^+$], 105 (24) [C$_7$H$_7$O$^+$], 121 (13) [C$_9$H$_{13}^+$], 163 (38) [M$^+$-C$_2$H$_3$O], 191 (2) [M$^+$-CH$_3$], 206 (7) [M$^+$].

Example 11

(r-8',c-10')-1-{Bicyclo[6.4.0]dodec-1'(12')-en-10'-yl}ethan-1-one (11)

The required diene starting material, 1-vinylcycloocte-1-ene, was synthesized according to W. Herz and R.-R. Juo [J. Org. Chem 1985, 50, 618].

3.60 ml (44.1 mmol) of but-3-en-2-one was added, with stirring, to a solution of 3.50 g (36.8 mmol) of 1-vinylcyclooct-1-ene in 40 ml of dry toluene. After cooling to 0° C., 0.41 g (3.05 mmol, 8 mol %) of aluminum trichloride was added thereto under nitrogen. After stirring at 0° C. for 15 minutes, the cooling bath was removed and the mixture was allowed to warm to room temperature. The mixture was then stirred at this temperature for 6 days under nitrogen and thereupon poured into 200 ml of water. The mixture was extracted three times with 200 ml of tert-butyl methyl ether per extraction. The combined organic extracts were dried over magnesium sulfate and the solvent was removed using a rotary evaporator. Flash chromatography (n-pentane/tert-butyl methyl ether, 50:1, $R_f$=0.46) on silica gel yielded 1.79 g (24%) of (r-8',c-10')-1-{bicyclo[6.4.0] dodec-1'(12')-en-10'-yl}ethan-1-one (11) as the main component in an admixture with the regioisomeric (r-8',c-9')-1-{bicyclo[6.4.0]dodec-1'(12')-en-9'-yl}ethan-1-one. Although both isomers have a similar smell, the odor of the mixture is determined by the more intensive (r-8',c-10')-1{-bicyclo[6.4.0]dodec-1'(12')-en-10'-yl}ethan-1-one (11).

Odor: Woody-fruity, ionone-like, Raldeine, Vertenex, cedar-like.—IR (film): ν=1709 cm$^{-1}$ (νOC=O);—$^1$H-NMR (CDCl$_3$): δ=1.33–1.72 (m, 11H, 2'-H, 4'-H$_2$-7'-H$_2$, 9'-H$_2$), 1.92–2.16 (m, 4H, 3'-, 11'-H$_2$), 2.18 (s, 3H, 2-H$_3$), 2.19–2.39 (m, 2H, 2'-,8'-H), 2.66 (m$_c$, 1H, 10'-H), 5.42 (t, J 3.1 Hz, 1H, 12'-H);—$^{13}$C-NMR data of the main isomer (CDCl$_3$): δ=24.64/25.17 (t, C-3',-6'), 25.93 (t, C-11'), 27.10/27.79 (t, C-4',-5'), 28.00 (q, C-2), 29.59 (t, C-7'), 32.62 (t, C-2'), 36.80 (t, C-9'), 38.17 (d, C-8'), 48.37 (d, C-10'), 120.24 (d, C-12'), 143.46 (s, C-1'), 211.98 (s, C-1);—MS (EI): m/z (%)=43 (100) [C$_2$H$_3$O$^+$], 55 (29) [C$_4$H$_7^+$], 67 (62) [C$_5$H$_7^+$], 81 (67) [C$_6$H$_9^+$], 91 (38) [C$_7$H$_7^+$], 107 (13)/121 (15) [C$_n$H$_{(2n-5)}^+$ series], 163 (30) [M$^+$-C$_2$H$_3$O], 191(3) [M$^+$-CH$_3$], 206 (6) [M$^+$]; —C$_{14}$H$_{22}$O (206.33): calc. C 81.50, H 10.75; found C 81.38, H 10.56.

The compounds of the following examples were synthesized from 1-vinylcyclooct-1-ene as set forth above. As these compounds also occur in admixture with the regioisomeric and diastereoisomeric Diels-Alder adducts some of the compounds, for unequivocal characterization, were purified micropreparatively and analyzed.

Example 12

(r-8', c-10')-1-{Bicyclo[6.4.0]dodec-1'(12')-en-10'-yl}methanal (12)

Odor: maritime, reminiscent of watermelons, tobacco and wood, somewhat ionone like-fruity and slightly ozone-like.—IR (film): ν=1724 cm$^{-1}$ (νCHO);—$^1$H-NMR (CDCl$_3$): δ=1.29–1.92 (m, 10H, 3'-H$_2$-6'-H$_2$,7'-,9'-H$_b$), 1.87 (m$_c$, 1H, 9'-H$_a$), 1.99 (ddd, J 13.8, 13.6, 3.1 Hz, 1H, 2'-H$_b$), 2.10 (m$_c$, 1H, 7'-H$_a$), 2.07–2.26 (m, 2H, 11'-H$_2$), 2.27 (m$_c$, 1H, 2'-H$_a$), 2.36 (m$_c$, 1H, 8'-H), 2.55 (m$_c$, 1H, 10'-H), 5.42 (t, J2.5 Hz, 1H, 12'-H), 9.70 (d,J 1.6 Hz, 1H, 1-H);—$^{13}$C-NMR data of the main isomer (C$_6$D$_6$): δ=24.68/25.54/25.38/26.28 (t, C-3'-C-6'), 25.45 (t, C-11'), 27.44 (t, C-7'), 28.33 (t, C-9'), 32.81 (t, C-2'), 38.12 (d, C-8'), 47.58 (d, C-10'), 120.43 (d, C-12'), 143.64 (s, C-1'), 202.72 (d, C-1);—MS (EI): m/z (%)=29 (10) [CHO$^+$], 41(32) [C$_3$H$_5^+$], 67 (26) [C$_5$H$_7^+$], 91 (100) [C$_7$H$_7^+$], 79 (45)/93 (34)/107 (41)/121 (33)/135 (14)/149 (6) [C$_n$H$_{(2n-5)}^+$ series], 192 (63) [M$^+$].

Example 13

(r-8',c-10')-1-{10'-Methylbicyclo[6.4.0]dodec-1'(12')-en-10'-yl}ethan-1-one (13)

Odor: woody-ionone like, creamy, warm, sweet, anber-like, after Iso E Super® and Vertofix®. Compared with the samples of the regioisomers and diastereoisomers, likewise obtained by preparative GC, compound 13 had the most interesting odor and the lowest threshold value.—IR (benzene): ν=1705 cm$^{-1}$ (νOC=O);—$^1$H-NMR (CDCl$_3$): δ=1.14 (s, 3H, 10'-Me), 1.34–1.73 (m, 8H, 3'-H$_2$-6'-H$_2$), 1.42(m$_c$, 1H, 7'-H$_b$), 1.52 (dd, J 13.0, 4.9 Hz, 1H, 9'-H$_b$), 1.66 (dd, J 13.0, 12.2 Hz, 1H, 9'-H$_a$), 1.83 (m$_c$, 1H, 7'-H$_a$), 1.89 (dd, 1H, J 15.0, 3.3 Hz, 1H, 11'-H$_b$), 1.99 (ddd, J 13.4, 12.5, 3.5 Hz, 1H, 2'-H$_b$), 2.17 (s, 3H, 2-Me), 2.26 (m$_c$, 1H, 2'-H$_a$), 2.29 (m$_c$, 1H, 8'-H), 2.31 (dd, 1H, J 15.0, 3.3 Hz, 1H, 11'-H$_a$), 5.37 (t, J 3.3 Hz, 1H, 12'-H);—$^{13}$C-NMR (CDCl$_3$): δ=20.26 (q, 10'-Me), 24.77 (q, C-2), 24.78/25.23 (t, C-3',-6'), 26.02/27.07 (t, C-4',-5'), 32.56 (t, C-2'), 32.78 (t, C-7'), 33.60 (t, C-11'), 34.47 (d, C-8'), 34.72 (t, C-9'), 46.65 (s, C-10'), 119.42 (d, C-12'), 142.04 (s, C-1'), 214.48 (s, C-1);—MS (EI): m/z (%)=43 (75) [C$_2$H$_3$O$^+$], 55 (37) [C$_4$H$_7^+$], 59 (58) [C$_3$H$_7$O$^+$], 67 (29) [C$_5$H$_7^+$], 81 (100) [C$_6$H$_9^+$], 95 (54) [C$_7$H$_{11}^+$], 107 (14)/121 (19)/135 (8)/149 (3) [C$_n$H$_{(2n-5)}^+$ series], 177 (30) [M$^+$-C$_2$H$_3$O], 205 (29) [M$^+$-CH$_3$], 220 (16) [M$^+$].

Example 14

(r-7',c-9')-1-{Bicyclo[5.4.0]undec-1'(11')-en-9'-yl}ethan-1-one (14)

Odor: sweet, ionone-like-fruity, woody-fresh, somewhat reminiscent of raspberry.—IR (film): ν=1709 cm$^{-1}$ (νOC=O);—$^1$H-NMR (CDCl$_3$): δ=1.36–1.88 (m, 10H, 3'-H$_2$-6'-H$_2$,8'-H$_2$), 2.08–2.22 (m, 4H, 2'-,10'-H$_2$), 2.17 (s, 3H, 2-H$_3$), 2.32 (m$_c$, 1H, 7'-H), 2.63 (dddd, J 12.0, 11.6, 5.7, 2.9 Hz, 1H, 9'-H), 5.41 (m$_c$, 1H, 11'-H);—$^{13}$C-NMR (CDCl$_3$): δ=26.30/27.32 (t, C-3',-5'), 27.86 (q, C-2), 29.85 (t, C4'), 31.13 (t, C-6'), 33.35/33.39 (t, C-8',-10'), 35.70 (t, C-2'), 39.21 (d, C-7'), 48.10 (d, C-9'), 120.34 (d, C-11'), 143.06 (s, C-1'), 211.68 (s, C-1);—MS (EI): m/z (%)=43 (24) [C$_2$H$_3$O$^+$], 55 (6) [C$_4$H$_7^+$], 67 (44) [C$_5$H$_7^+$], 91 (44) [C$_7$H$_7^+$], 79 (18)193 (16)/107 (12)/121 (8) [C$_n$H$_{(2n-5)}^+$ series], 149 (100) [M$^+$-C$_2$H$_3$O], 159 (3) [M$^+$-CH$_3$-H$_2$O], 177 (14) [M$^+$-CH$_3$], 192 (34) [M$^+$].

Example 15

Feminine Extrait Perfume with Compound 3

| | Compound/ingredient | Weight content (%) |
|---|---|---|
| 1. | Ambrarome | 15 |
| 2. | Cedarwood Oil Virginia | 50 |
| 3. | Citronellol Extra | 30 |
| 4. | Cyclopentadecanolide (Thibetolide) | 50 |
| 5. | 4-(1-Ethoxyethenyl)-3,3,5,5-Tetramethyl-Cyclohexanone (Kephalis) | 40 |
| 6. | 2-Ethyl-6,6-Dimethylcyclohex-2-Ene-Carboxylic Acid Ethyl Ester(Givescone) | 15 |
| 7. | Ethyl Linalool | 50 |
| 8. | Eugenol Pure | 30 |
| 9. | 3-(4-Methoxyphenyl)-2-Methylpropanal | 60 |
| 10. | 1,2,3,5,6,7-Hexahydro-1,1,2,3,3-Pentamethyl-4h-Indenone (Cashmeran) | 15 |
| 11. | Indole 10% Dpg | 2 |

-continued

| Compound/ingredient | | Weight content (%) |
|---|---|---|
| 12. | Isoambrettolide (Ambrettolide) | 15 |
| 13. | Cumin Oil Roman 10% Dpg | 4 |
| 14. | Linalyl Acetate Synthetic | 30 |
| 15. | Mandarine Oil | 20 |
| 16. | Methyl Anthranilate 10% Dpg | 3 |
| 17. | Methylionone (Isoraldeine 95) | 120 |
| 18. | Nectaryl | 10 |
| 19. | 3-Methyl-5-(2,2,3-Trimethylcycopent-3-En-1-Yl)Pentan-2-Ol (Sandalore) | 90 |
| 20. | Olibanum Oil Pure | 5 |
| 21. | Patchouli Oil Pure | 40 |
| 22. | Phenylethyl Alcohol Extra | 32 |
| 23. | Rose Oil | 2 |
| 24. | Vanillin | 4 |
| 25. | Compound 3 | 250 |
| 26. | Juniper Berry Oil | 10 |
| 27. | Ylang-Ylang Oil Extra | 5 |
| 28. | Cinnamaldehyde | 3 |
| | | 1000 |

Compound 3 forms, together with methylionone, patchouli, Sandalore and Thibetolide/Ambrettolide, the main accord of this modern, monolithic feminine-woody chypre perfume. In spite of the high dosage of 25%, the composition remains harmonic and transparent, and lives by the cedar-like-amber-like, pleasant warmth of compound 3. This already unfolds refreshingly in the aromatic scent and develops into a spicy-floral bouquet which is long-lasting.

In olfactory intensity, diffusion and adhesive resistance, compound 3 in the same dosage is clearly superior to the odorants Iso E Super® and Vertofix® in this composition.

Example 16

Perfume Oil for Conditioner with Compound 3

| Compound/ingredient | | Weight content (%) |
|---|---|---|
| 1. | Amyl salicylate | 50 |
| 2. | Benzyl alcohol extra | 100 |
| 3. | Citronellol extra | 50 |
| 4. | Coumann pure crystalline | 20 |
| 5. | Cyclopentadecanolide (thibetolide) | 30 |
| 6. | 2-methyl-3-[4-(1,1-dimethyl)ethyl]-phenyl-propanal (lilial) | 250 |
| 7. | Dynascone 10 | 1 |
| 8. | 3-(4-ethylphenyl)-2,2-dimethylpropanal (floralozone) | 4 |
| 9. | 2-ethyl-4-(2,2,3-trimethylcyclopent-3-en-1-yl)-but-2-en-1-ol (radjanol) | 10 |
| 10. | Alpha-hexylcinnamaldehyde | 150 |
| 11. | Linalool synthetic | 100 |
| 12. | Para-methylacetophenone | 5 |
| 13. | Methylionone (isoraldeine 70) | 100 |
| 14. | Phenylethyl acetate | 30 |
| 15. | Terpineol pure | 50 |
| 16. | Compound 3 | 50 |
| | | 1000 |

Compound 3 confers to the composition a pleasant, fresh-dry note with a soft, frankincense note, which underlines the soft caring character of the product. It rounds off the composition, has a very good adhesion to the washing and has a fixative action on the remaining odorants.

Example 17

Floral-maritime Perfume Composition with Compound 2

| Compound/ingredient | | Weight content (%) |
|---|---|---|
| 1. | Bergamot oil | 100 |
| 2. | Lemon oil italian pure | 20 |
| 3. | Allyl 3-cyclohexylpropionate 10% dpg | 5 |
| 4. | Alpha-damascone 10% dpg | 3 |
| 5. | 2,6-dimethylheptan-2-ol | 1 |
| 6. | 1,1-dimethyl-3-phenylpropanol | 3 |
| 7. | Dipropylene glycol (dpg) | 90 |
| 8. | Ethyl linalool | 85 |
| 9. | Geraniol pure | 1 |
| 10. | 1,3,4,6,7,8-hexahydro-4,6,6,7,8,8-hexamethyl-cyclopenta[g]-2-benzopyran (galaxolide) 50 bb | 140 |
| 11. | Beta-ionone synthetic | 2 |
| 12. | Linalool synthetic | 35 |
| 13. | Linalyl acetate synthetic | 15 |
| 14. | 7-methyl-2h-benzo-1,5-dioxepin-3(4h)-one (calone 1951) | 6 |
| 15. | 2-methyl-3-[4-(1,1-dimethyl)ethyl]-phenylpropanal (lilial) | 120 |
| 16. | Methyldihydrojasmonate (cepionat) | 320 |
| 17. | Nona-2(e),6(z)-dienal 10%/tec 10% dpg | 5 |
| 18. | Phenylacetaldehyde (hyacinth aldehyde) 85%/pea 10% dpg | 5 |
| 19. | Alpha-terpineol (lindenol) | 2 |
| 20. | Gamma-undecalactone (peach pure) | 2 |
| 21. | Compound 2 | 40 |
| | | 1000 |

Compound 2 shapes the floral-maritime note of this perfume composition, and also confers to it fruity-ionone-like aspects and a pleasant tobacco-like note. It fixes and harmonizes the creation by its floral, maritime and woody facets and brings naturalness and transparency into the modern "aqueous-flowery" perfumistic theme.

Example 18

Floral Hesperidic Note with Compound 2

| Compound/ingredient | | Weight content (%) |
|---|---|---|
| 1. | Mugwort oil 10% dpg | 6 |
| 2 | Bergamot oil | 70 |
| 3 | Cardamon oil ceylon | 15 |
| 4. | Cedarwood oil brown virginian | 150 |
| 5. | Citronellol extra | 20 |
| 6. | Coriander oil | 2 |
| 7. | Coumarin pure crystalline | 2 |
| 8. | Cumin oil (roman cumin oil) 10% dpg | 5 |
| 9. | Cypress oil | 3 |
| 10. | 2,4-dihydroxy-3,6-dimethylbenzoic acid methyl ester (evernyl) 10% dpg | 5 |
| 11. | Dipropylene glycol (dpg) | 109 |
| 12. | Ethyl linalool | 45 |
| 13. | (3z)-hex-3-en-1-ol 10% dpg | 5 |
| 14. | Alpha-hexylcinnamaldehyde | 17 |
| 15. | Beta-ionone synthetic | 30 |
| 16. | Mace oil (nutmeg oil) usp | 10 |
| 17. | Mandarine oil yellow italian | 10 |
| 18. | Methyldihydrojasmonate (cepionate) | 120 |
| 19. | Muscone 10% dpg | 6 |
| 20. | Orange oil bitter | 10 |

-continued

| Compound/ingredient | Weight content (%) |
|---|---|
| 21. 2-phenylethan-1-ol white | 10 |
| 22. Compound 2 | 350 |
| | 1000 |

Compound 2 increases the intensity and the character of the perfume, emphasizes the fresh-hesperidic like facets and reduces the dry-woody elements.

The invention being thus described, it will be obvious that the same may be viewed in many ways. Such variations are not to be regarded as a departure from the spirit and scope of the invention and all such modifications are intended to be included within the scope of the following claims.

What is claimed is:

1. A compound of formula (I):

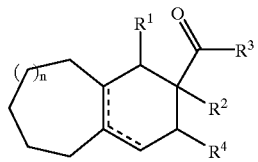

I wherein
n is 1 or 2;
$R^1$ and $R^4$ are independently H or $CH_3$; and
$R^2$ and $R^3$ are independently H, $CH_3$ or $CH_2CH_3$;
with the excemtion of a compound wherein n=1, $R^1=R^2=R^4=H$, and $R^3=CH_2CH_3$.

2. A compound according to claim 1 having formula (I'):

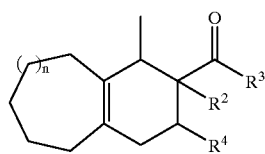

I' wherein
n is 1 or 2;
$R^4$ is H or $CH_3$; and
$R^2$ and $R^3$ are independently H, $CH_3$ or $CH_2CH_3$.

3. A compound according to claim 1 selected from the group consisting of 1-{bicyclo[6.4.0]dodec-1'(8')-en-10'-yl}ethan-1-one (1), 1{bicyclo[6.4.0]dodec-1'(8')-en-10'-yl}methanal (2), 1-{9',10'-dimethylbicyclo[6.4.0]dodec-1'(8')-en-10'-yl}ethan-1-one (3), 1-{8',9'-dimethylbicyclo[5.4.0]undec-1'(7')-en-9'-yl}ethan-1-one (4), 1-{9'-methylbicyclo[6.4.0]dodec-1'(8')-en-10'-yl}ethan-1-one (5), 1-{10'-methylbicyclo[6.4.0]dodec-1'(8')-en-10'-yl}methanal (6), 1-{11'-methylbicyclo[6.4.0]dodec-1'(8')-en-10'-yl}ethan-1-one (7), 1-{bicyclo[6.4.0]dodec-1'(8')-en-10'-yl}propan-1-one (8), 1-{9',11'-dimethylbicyclo[6.4.0]dodec-1'(8')-en-10'-yl }ethan-1-one (9), 1-{8'-methylbicyclo[5.4.0]undec-1'(7')-en-9'-yl}ethan-1-one (10), 1-{bicyclo[6.4.0]dodec-1'(12')-en-10'-yl}ethan-1-one (11), 1-{bicyclo[6.4.0]dodec-1'(12')-en-10'-yl}methanal (12), 1-{10'-methylbicyclo[6.4.0]dodec-1'(12')-en-10'-yl}ethan-1-one (13) and 1-{bicyclo[5.4.0]undec-1'(11')-en-9'-yl}ethan-1-one (14).

4. A compound according to claim 2 selected from the group consisting of 1-{9',10'-dimethylbicyclo[6.4.0]dodec-1'(8')-en-10'-yl}ethan-1-one (3), 1-{(8',9'-dimethylbicyclo[5.4.0]undec-1'(7')-en-9'-yl}ethan-1-one (4), 1-{9'-methylbicyclo[6.4.0]dodec-1'(8')-en-10'-yl}ethan-1-one (5) and 1-{8'-methylbicyclo[5.4.0]undec-1'(7')-en-9'-yl}ethan-1-one (10).

5. A compound according to claim 3 selected from the group consisting of 1-{(bicyclo[6.4.0]dodec-1'(8')-en-10'-yl}methanal (2) and 1-{10'-methylbicyclo[6.4.0]dodec-1'(8')-en-10'-yl}methanal (6).

6. A compound according to claim 3 selected from the group consisting of 1-{bicyclo[6.4.0]dodec-1'(8')-en-10'-yl}methanal (2) and 1-{9',10'-dimethylbicyclo[6.4.0]dodec-1'(8')-en-10'yl}ethan-1-one (3).

7. A compound according to claim 3 selected from the group consisting of 1-{bicyclo 6.4.0]dodec-1'(12')-en-10'-yl}ethan-1-one (11), 1-{bicyclo[6.4.0]dodec-1'(12')-en-10'-yl}methanal (12), 1-{10'-methylbicyclo[6.4.0]dodec-1'(12')-en-10'-yl}ethan-1-one (13) and 1-{bicyclo[5.4.0]undec-1'(11')-en-9'-yl}ethan-1-one (14) in admixture with theirs corresponding regioisomeric Diels-Alder adducts.

8. An odorant composition comprising at least one compound of formula I:

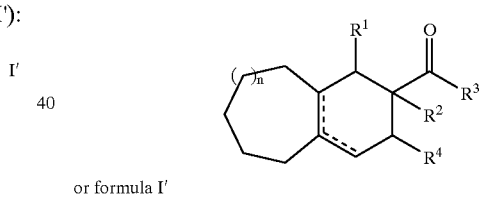

I or formula I'

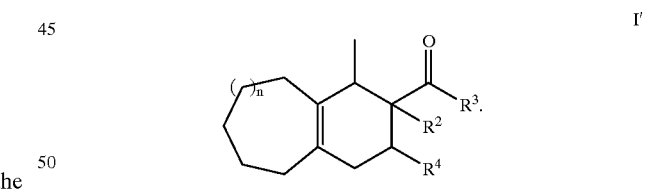

I'

9. A process for producing a $R^1$-methyl substituted compound of formula (I')

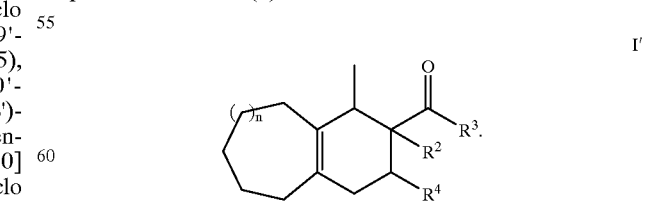

I' comprising reacting a spirocyclic vinylcyclopropane compound with a dienophile in the presence of a catalyst; and producing regioselectively or Z-diastereoselectively, the compound of formula (I').

10. A process according to claim 9 wherein the vinylcyclopropane compound is 4-methylenespiro[2.6]nonane.

11. A process according to claim 9 wherein the vinylcyclopropane compound is 4-methylenespiro[2.7]decane.

12. A process according to claim 9 wherein the dienophile is 3-methyl-3-buten-2-one.

13. A process according to claim 9 wherein the catalyst is $(Ph_3P)_3RhCl$.

14. A 4-Methylenespiro[2.6]nonane compound.

15. An odorant composition comprising 4-Methylenespiro[2.6]nonane.

* * * * *